(12) United States Patent
Joseph et al.

(10) Patent No.: US 9,597,238 B2
(45) Date of Patent: *Mar. 21, 2017

(54) VOLUME INDICATORS WITH MASKING LAYER

(71) Applicant: The Procter & Gamble Company, Cincinnati, OH (US)

(72) Inventors: Laveeta Joseph, Cincinnati, OH (US); Thomas James Klofta, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 42 days.

This patent is subject to a terminal disclaimer.

(21) Appl. No.: 14/663,480

(22) Filed: Mar. 20, 2015

(65) Prior Publication Data

US 2015/0265477 A1 Sep. 24, 2015

Related U.S. Application Data

(60) Provisional application No. 61/955,829, filed on Mar. 20, 2014.

(51) Int. Cl.
*A61F 13/42* (2006.01)
*A61F 13/84* (2006.01)
*A61F 13/513* (2006.01)
*A61F 13/514* (2006.01)

(52) U.S. Cl.
CPC .............. *A61F 13/84* (2013.01); *A61F 13/42* (2013.01); *A61F 13/51394* (2013.01); *A61F 13/51496* (2013.01); *A61F 2013/422* (2013.01); *A61F 2013/426* (2013.01); *A61F 2013/427* (2013.01)

(58) Field of Classification Search
CPC ................ A61F 13/42; A61F 2013/422; A61F 2013/427; A61F 2013/429; A61F 2013/8497
See application file for complete search history.

(56) References Cited

U.S. PATENT DOCUMENTS

| 4,022,211 A | 5/1977 | Timmons et al. |
| 4,743,238 A | 5/1988 | Colon et al. |
| 5,690,624 A | 11/1997 | Sasaki et al. |
| 5,766,212 A * | 6/1998 | Jitoe ...................... A61F 13/42 604/361 |
| 5,823,891 A | 10/1998 | Winskowicz |

(Continued)

FOREIGN PATENT DOCUMENTS

| WO | WO 94/10958 | 5/1994 |
| WO | WO 03/070138 | 8/2003 |

(Continued)

OTHER PUBLICATIONS

International Search Report, PCT/US2015/021685, mailed Jun. 25, 2015, 10 pages.

*Primary Examiner* — Lynne Anderson
(74) *Attorney, Agent, or Firm* — Kathleen Y. Carter

(57) ABSTRACT

An absorbent article comprising a topsheet, a backsheet, and an absorbent core disposed between the topsheet and the backsheet, wherein the article further comprises at least two volume indicators, and wherein at least one volume indicator comprises a masking layer comprising a water-soluble colorant and a stationary color layer comprising a permanent colorant.

24 Claims, 5 Drawing Sheets

(56) References Cited

U.S. PATENT DOCUMENTS

| | | |
|---|---|---|
| 5,897,541 A | 4/1999 | Uitenbroek et al. |
| 5,938,544 A | 8/1999 | Winskowicz et al. |
| 6,277,037 B1 | 8/2001 | Winskowicz et al. |
| 6,297,424 B1 | 10/2001 | Olson et al. |
| 6,358,160 B1 | 3/2002 | Winskowicz |
| 6,596,918 B1 * | 7/2003 | Wehrle ............... A61F 13/42 604/361 |
| 6,710,221 B1 | 3/2004 | Pierce et al. |
| 6,747,185 B2 | 6/2004 | Inoue et al. |
| 6,772,708 B2 | 8/2004 | Klofta et al. |
| 6,904,865 B2 | 6/2005 | Klofta et al. |
| 7,159,532 B2 | 1/2007 | Klofta et al. |
| 7,306,764 B2 | 12/2007 | Mody |
| 7,429,688 B2 * | 9/2008 | Yoshioka ............ A61F 13/42 442/118 |
| 7,829,181 B2 | 11/2010 | Macdonald et al. |
| 7,834,234 B2 | 11/2010 | Roe et al. |
| 7,838,720 B2 | 11/2010 | Roe et al. |
| 8,080,704 B2 | 12/2011 | Uchida et al. |
| 8,273,306 B2 | 9/2012 | Song et al. |
| 2003/0154904 A1 | 8/2003 | Klofta et al. |
| 2005/0124947 A1 | 6/2005 | Fernfors |
| 2005/0234414 A1 | 10/2005 | Liu |
| 2006/0224132 A1 | 10/2006 | Roe et al. |
| 2006/0229577 A1 | 10/2006 | Roe et al. |
| 2006/0229578 A1 | 10/2006 | Roe et al. |
| 2009/0326491 A1 | 12/2009 | Long et al. |
| 2010/0030173 A1 | 2/2010 | Song et al. |
| 2010/0168700 A1 * | 7/2010 | Schmidt ............... A61F 13/42 604/361 |
| 2010/0262099 A1 | 10/2010 | Klofta |
| 2010/0262100 A1 | 10/2010 | Klofta |
| 2011/0137274 A1 | 6/2011 | Klofta et al. |
| 2012/0157948 A1 | 6/2012 | Nhan et al. |
| 2013/0116644 A1 | 5/2013 | Wei et al. |
| 2013/0158493 A1 * | 6/2013 | De Bruin ............. A61L 15/56 604/361 |
| 2013/0289508 A1 * | 10/2013 | Wei ..................... A61F 13/42 604/361 |
| 2015/0265475 A1 * | 9/2015 | Joseph ............ A61F 13/51496 604/361 |

FOREIGN PATENT DOCUMENTS

| | | |
|---|---|---|
| WO | WO 2005/102238 | 11/2005 |
| WO | WO 2009/152021 | 12/2009 |
| WO | WO 2010/001274 | 1/2010 |
| WO | WO 2013/038278 | 3/2013 |
| WO | WO 2013/088273 | 6/2013 |

\* cited by examiner

VOLUME INDICATORS WITH MASKING LAYER

FIELD OF THE INVENTION

The present invention relates to disposable absorbent articles with volume indicators.

BACKGROUND OF THE INVENTION

Disposable absorbent articles may be used by infants, toddlers, and incontinent individuals to receive and contain body exudates. Some disposable absorbent articles may provide an indicator feature, such as a wetness indicator. A wetness indicator can allow a caregiver to know when the wearer has urinated and/or soiled the article. A prompt removal of the wet absorbent article may help prevent a number of skin or health issues that may result from or be exacerbated by prolonged exposure of the skin to moisture.

Many wetness indicators are binary. That is, the wetness indicator may be one color when dry and then triggered to become another color by any wetness in the article, even with a very small amount. This may be sufficient and even good for small children who have sensitive skin or need to be carefully monitored to insure they are fully hydrated. For larger children, an absorbent article may contain some wetness and yet not urgently need to be changed. For such a circumstance, a wetness indicator that has been triggered may not necessarily be very helpful to the caregiver, who might not desire to change the article until several insults have occurred.

In some circumstances, it would be more helpful to the caregiver for an absorbent article to have a volume indicator, that is, some indication that the article has reached a certain load. Some volume indicators may be location-based wetness indicators. For example, as multiple insults occur, the wetness may be forced to travel further from its original source, and once a particular location indicates wetness, the caregiver may know that a certain volume has been released into the article. The problem with some location-based volume indicators is that their accuracy may not be reliable, as they can be dependent on the positioning of the article on the wearer during insult (sleeping vs sitting vs standing vs crawling). In addition, results may vary according to the gender of the wearer.

These and other difficulties mean that there is a continuing need for volume indicators that can be a reliable gauge of the volume of liquid that the absorbent article is holding, independent of the wearer.

SUMMARY OF THE INVENTION

An absorbent article comprising a topsheet, a backsheet, and an absorbent core disposed between the topsheet and the backsheet, wherein the article further comprises at least two volume indicators, and wherein at least one volume indicator comprises a masking layer comprising a water-soluble colorant and a stationary color layer comprising a permanent colorant.

DETAILED DESCRIPTION OF THE INVENTION

Definitions

Figure 1:
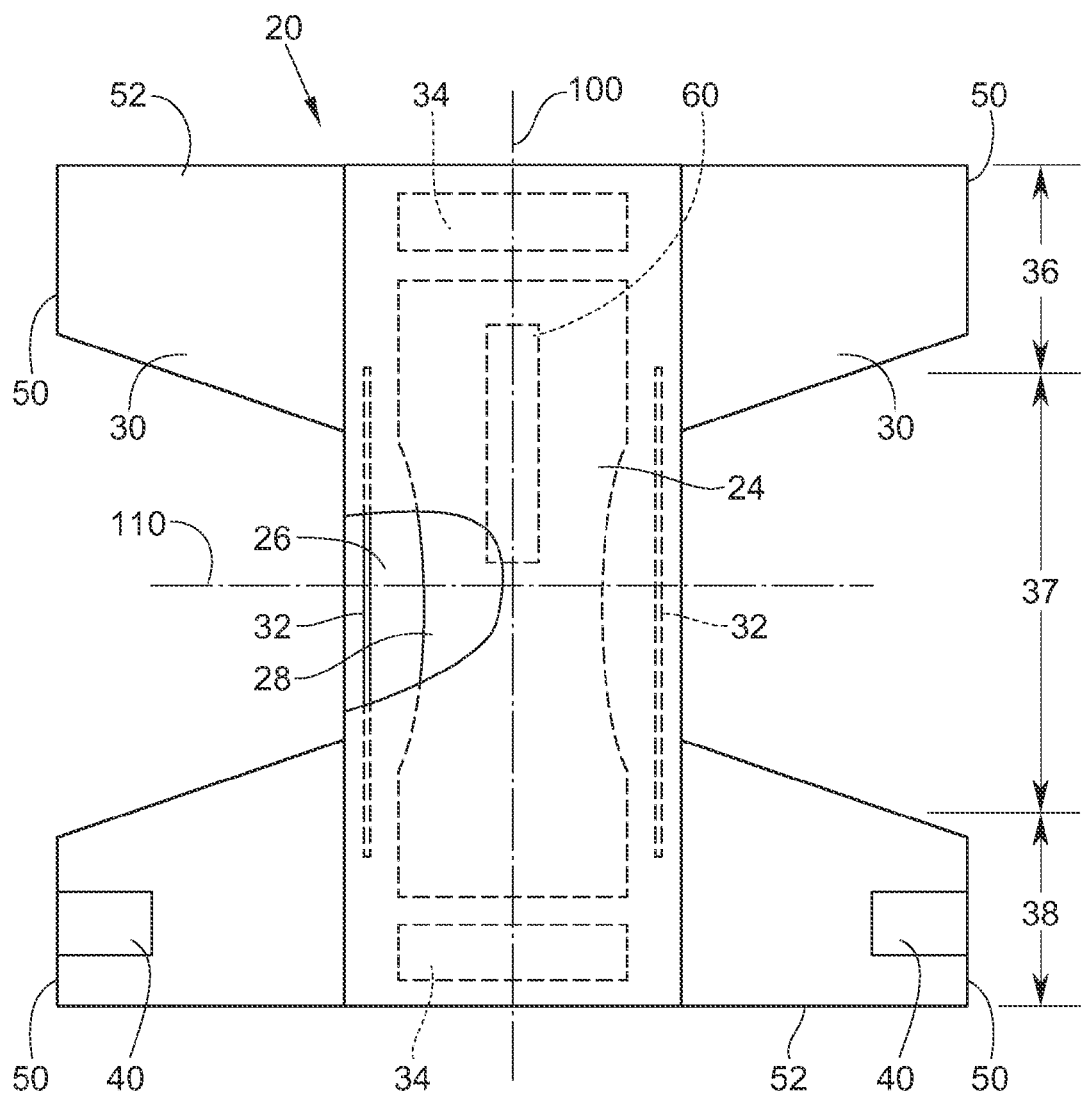
FIG. 1 shows a cut away view of a disposable absorbent article in a flattened, uncontracted condition, the disposable absorbent article comprising at least one volume indicator in accordance with the present invention.

As used herein, the term "absorbent article" refers to garments generally worn by infants/toddlers/adults and other incontinent individuals to absorb and contain urine, feces and/or menses. It should be understood, however, that the term absorbent article is also applicable to other garments such as training pants, incontinent briefs, feminine hygiene garments or panties, and the like. In some embodiments, "absorbent article" may refer to a taped diaper.

As used herein, the term "colorant" refers to any dye, ink, pigment, inks that comprise dyes or pigments, pH indicators, metal indicators, oxidation or reduction indicators, solvachromic colorants, biological colorant indicators that change color upon contact with a biological component of an exudates, or any material that has the effect of changing the color of its environment, or any combination thereof.

As used herein, the term "permanent colorant" refers to a colorant that maintains its color independent of environmental factors or one that does not change its color under any circumstance, such as a pH change or exposure to a liquid or specific components of the liquid, high humidities, or high or low temperatures.

DESCRIPTION

The present invention relates to indicators that are based on the volume of fluid the indicator is exposed to, as measured via color change. Many traditional wetness indicators use pH-based triggering chemistries or water soluble dyes/inks, in which the dry wetness indicator begins at an initial color and when wetted by urine/fluid, changes to a different color within a few minutes irrespective of the volume of fluid contacting it. In the present invention, the mechanism that triggers the color change is not necessarily a pH change alone or solubility in fluid/urine, but rather one in which the volume of fluid determines whether the indicator changes color and the rate of the color change. In some embodiments, the structure of the indicator, comprising a masking layer and/or a barrier layer, delays or allows a gradual reveal of the color change. That is, the colorants may not be activated to a second color and/or made visible until a certain volume of fluid is released and contacts the indicator. This in turn allows for indicators that can show not only how much fluid has been released, but in some cases, how long since the fluid has been released. And rather than being simply a binary indicator, that is one color when dry and another color when wet, the indicators of the present invention may show gradations/hues of color between the first and second color states.

In some embodiments, an absorbent article may comprise multiple volume indicators that comprise colorants that are water soluble or are released upon contact with fluid. In some embodiments, a particular volume indicator may change colors or become visible/invisble through the utilization of liquid-activatable colorants which are activated through the infusion of fluid into a barrier layer that initially bars access of the liquid. In some embodiments, the liquid-activatable colorants are encapsulated dye particles.

In the case of multiple volume indicators, one volume indicator may change colors quickly, within about 15-30 minutes of an insult of urine, while a second volume indicator may not change colors until a much longer duration, in the range of about 1 hour to about 4-12 hours of exposure to body exudates. The time difference for the two color changes may be due to the amount or thickness of the masking or barrier layer.

Absorbent Article

FIG. 1 is a plan view of an article, in this case a diaper 20, of the present invention in a flat, uncontracted state with portions of the structure being cut away to more clearly show the construction of the diaper. The portion of the diaper 20 that faces a wearer is oriented towards the viewer. As shown in FIG. 1, the diaper 20 comprises a topsheet 24; an outer cover 26; an acquisition layer (not shown), and an absorbent core 28 that is positioned between at least a portion of the topsheet 24 and the backsheet 26. The absorbent article further comprises side panels 30, elasticized leg cuffs 32, elastic waist features 34, and a fastening system generally designated 40. The diaper 20 has a first waist region 36, a second waist region 38 opposed to the first waist region 36, and a crotch region 37 located between the first waist region 36 and the second waist region 38. The periphery of the diaper 20 is defined by the outer edges of the diaper 20 in which longitudinal edges 50 run generally parallel to a longitudinal centerline 100 of the diaper 20 and end edges 52 run between the longitudinal edges 50 generally parallel to a lateral centerline 110 of the diaper 20.

The outermost surface of the backsheet/outer cover 26 forms the garment contacting surface (not shown) of the diaper 20, while the innermost surface of the topsheet 24 forms the body contacting surface (not shown) of the diaper 20. The absorbent articles of the present invention comprise a topsheet 24. In one example, the topsheet 24 is compliant, soft feeling, and non-irritating to the wearer's skin. It can be elastically stretchable in one or two directions. Further, the topsheet is liquid pervious, permitting liquids (e.g., menses, urine, and/or runny feces) to readily penetrate through its thickness. A suitable topsheet can be manufactured from a wide range of materials such as woven and nonwoven materials; apertured or hydroformed thermoplastic films; porous foams; reticulated foams; reticulated thermoplastic films; and thermoplastic scrims. Suitable woven and non-woven materials may comprise of natural fibers such as wood or cotton fibers; synthetic fibers such as polyester, polypropylene, or polyethylene fibers; or combinations thereof. If the topsheet includes fibers, the fibers may be spunbond, carded, wet-laid, meltblown, hydroentangled, or otherwise processed as is known in the art.

In one embodiment, the backsheet 26 is impervious to fluids (e.g., menses, urine, and/or runny feces) and is manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent article from wetting articles which contact the absorbent article such as bedsheets, pants, pajamas and undergarments. The backsheet 26 may thus comprise a woven or nonwoven material, polymeric films such as thermoplastic films of polyethylene or polypropylene, and/or composite materials such as a film-coated nonwoven material (i.e., having an inner film layer and an outer nonwoven layer). The backsheet 26 and the topsheet 24 are positioned adjacent a garment surface and a body surface, respectively, of the absorbent core 28.

The articles of the present invention additionally comprise one or more absorbent cores 28. The absorbent core 28 is at least partially disposed between the topsheet and the backsheet and may take on any size or shape that is compatible with the disposable absorbent article. The absorbent core 28 may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials (AGM); or any equivalent material or combinations of materials, or mixtures of these. Further useful materials and constructions appropriate for the topsheets, backsheets, outer covers, and absorbent cores described herein may be found in U.S. Ser. No. 14/302,473.

The articles of the present invention may comprise at least one graphic, which refers to images or designs that are constituted by a figure (i.e., a line(s)), a symbol or character, a color difference or transition of at least two colors, or the like. The graphic may have an aesthetic image or design that can provide certain benefits when the absorbent article of the invention is viewed by users or consumers. A variety of graphics can be used in the absorbent articles of the invention.

The disposable absorbent articles of the present invention further comprise at least one volume indicator 60. A volume indicator can be located on or against any surface of a component material, including the body contacting surface and the garment contacting surface provided that the volume indicator 60 remains visible from the exterior of the absorbent article. Non-limiting examples of the component material include the backsheet film/NW, the topsheet, the acquisition layer, the absorbent core, and the barrier leg cuffs. In another embodiment, a volume indicator 60 is disposed between the absorbent core and the backsheet and in liquid communication with the absorbent core.

Masking Layer

Figure 2:
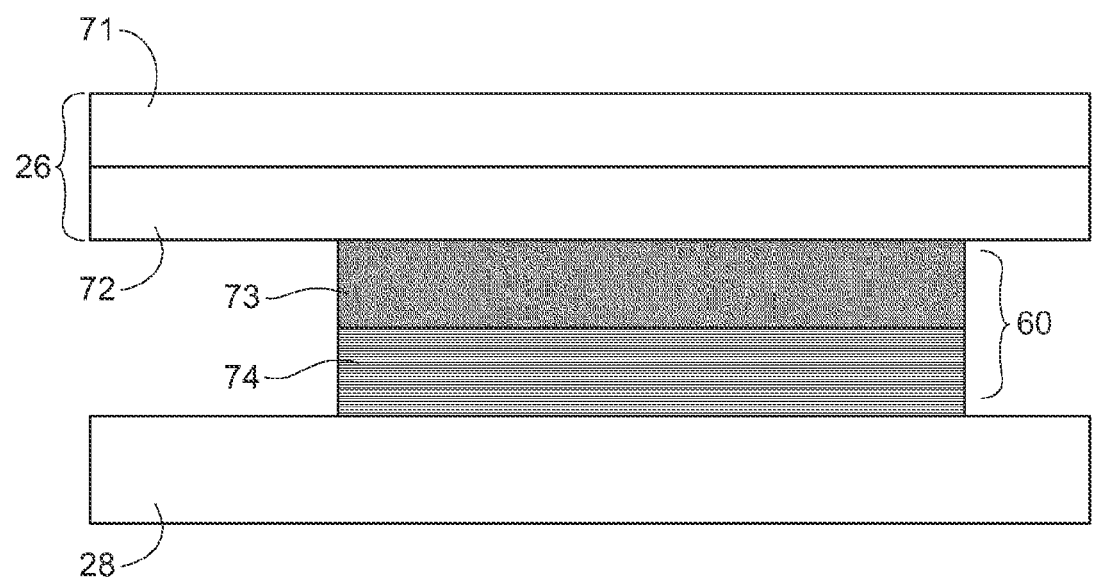
FIG. 2 shows an embodiment of a volume indicator of the present invention.

The absorbent article may comprise at least one volume indicator. In some embodiments, a volume indicator may comprise a masking layer. One such embodiment is schematically shown in FIG. 2. The outer cover 26 is furthest away from the wearer and consists of an outer cover nonwoven layer 71 (farthest away from the wearer) and a backsheet film 72 (inside from the outer cover nonwoven). The next layer towards the interior of the article is the volume indicator, 60, comprising a masking layer 73 next to the backsheet film and a stationary color layer 74 that is next to the article's absorbent core 28.

The stationary color layer may comprise one or more of a permanent colorant, a water-insoluble colorant, a solvent-soluble colorant which is more soluble in organic lipophilic chemistries like mineral oil, a pH indicator layer, or an encapsulated colorant, each of which stay in the matrix and do not dissolve into the core. The stationary color layer as a whole may or may not be a permanent or fixed color, that is, a colorant or colorants that are one color and never change irrespective of changes in the environment. In all cases, the stationary color layer stays within its matrix layer throughout the entire use of the article and does not migrate into the core or the adjacent layers. The stationary color layer may also comprise porosigens to alter the fluid flow of the layer which in turn regulates the rate of color change of the volume indicator.

The masking layer may comprise a permanent colorant, which, in some embodiments, may be a dark color. The masking layer may also comprise a colorant that is a water/pH-activated colorant or an encapsulated colorant. The masking layer may comprise a pH indicator or a dispersed/encapsulated solid colorant that dissolves when wetted with exudates, is activated by metals in the exudates, or is activated by oxidation or reduction reactions. The masking layer may comprise a pH indicator, a water-soluble, solvent-soluble, and/or a polar colorant(s), that may be in encapsulated form or any combinations thereof.

The initial color of the volume indicator may be the color or design of the masking layer or may be the color due to the combination of the color of the masking layer and the stationary color layer. The thickness, composition, pattern design, and placement of both the masking layer and stationary color layer help determine the initial color intensity and the rate of change to the final color of the volume indicator. The rate of color change of the volume indicator is also dependent on the porosity of the stationary color layer.

There are several mechanisms that may happen when an insult occurs, depending on the constitution of the masking and stationary color layers. In a first option, the masking layer may be a water-soluble colorant(s) in combination with other colorants while the stationary color layer may be a porous insoluble colorant(s) or pH indicator(s). Upon insult, the urine is gathered in the article's absorbent core. As the core becomes wet, the wetness permeates into the volume indicator, that is, into the porous stationary color layer and then into the masking layer. The stationary color layer is porous enough to enable the colorant from the masking layer to permeate through the stationary color layer and into the core. The colorant in the stationary color layer may be in an encapsulated form or may be water insoluble or a pH indicator bound to the stationary layer matrix, to enable the colorants to stay in place as the water permeates the layer. So while the initial color of the volume indicator is the color of the masking layer or the combination of the masking layer and the stationary color layer, the masking layer water-soluble colorant(s) is absorbed into the core and the final color of the volume indicator is the final color of the stationary color layer or a combination of the final color of the colorants remaining in the masking layer without the water soluble colorant(s) and the final color of the stationary layer. The porosity and composition of the stationary colorant layer regulates the rate of colorant absorption into the core from the masking layer and the rate of color change. When the colorant in the stationary color layer is a pH indicator, the stationary color layer may be an adhesive matrix, such as those described in U.S. Pat. No. 6,772,708. In other embodiments, the stationary color layer may be an ink matrix where the colorant is applied on the masking layer on top of the film made up of acrylic or acrylic-styrene polymers with the optional inclusion of surfactants to enhance the rate of exudates flow from the core.

In a second option, the masking layer (water-soluble colorants and combination of other colorants) and the stationary color layer (porosigens, pH indicators and water-insoluble colorants) may initially be mixed into one layer. The final result is the same as in option 1, where the final color is the color of the remaining water insoluble colorants and/or final pH indicator color or combinations thereof. The relative amounts of the masking layer water-soluble colorant(s) and the stationary color layer colorant(s) as well as the compositions of these layers and their thicknesses along with their design and placement all determine the initial color of the volume indicator and the rate of the color change.

In third and fourth options, there may be multiple stationary color layers (to adjust porosity) or multiple masking layers (to adjust the masking layer water soluble colorant disappearing rate). In general, the relative amounts, compositions, pattern designs, placements/locations of, and thicknesses of the masking and stationary color layers determine the initial color of the volume indicator and the rate of color change for the volume indicator upon exposure to fluid.

A volume indicator may or may not change colors quickly. One advantage of the present invention is that a volume indicator may change colors gradually over time, giving a continuing indication of how saturated and full the article is. That is, as the masking layer water soluble colorant(s) is absorbed into the core, the volume indicator color may have intermittent colors between the original and final states. Or the volume indicator may have a spotted or mottled appearance as some but not all of the masking layer colorant is absorbed into the core.

In an article with multiple volume indicators, one of the volume indicators may be made to preferentially change color first by making the stationary color layer very thin to allow quick diffusion of the urine to the masking layer or by increasing the relative porosity of the stationary layer. Optionally, a surfactant wetting agent could be added to the porous stationary color layer to speed up the rate of absorption of the urine to allow its migration to the masking layer. In addition, the first volume indicator could be preferentially located in close proximity to the "pee point" to enhance the absorption of the first urination of the wearer. Preferential absorption of the urine or exudates by the first volume indicator could also be motivated by varying the amount of AGM (like channels and no-channel regions) between the article core and the porous stationary color layer such that more urine would come in contact with the first volume indicator at a faster time than the other volume indicators. The concentration of the AGM would have to be optimized so not to hinder migration through the stationary color layer. The AGM might also be replaced by a porous and sponge-like layer made of polyester or other polar polymers known in the art. In addition, the migration of the masking layer colorant into the core could be sped up by reducing the colorant concentration, adding a super-wetting surfactant in the masking layer, or by adding porosigens like sodium chloride to create void spaces and pathways for fluid flow after wetting from urine/exudates. Some representative examples of porosigens that can be utilized include inorganic salts like sodium chloride, potassium chloride, magnesium chloride, trisodium phosphate, ammonium dihydrogen phosphate, and disodium sulfate, fruit acids like citric acid, tartaric acid, malonic acid, gluconic acid, and maleic acid, the conjugate bases of fruit acids like sodium citrate, magnesium citrate, and potassium tartrate, opacifiers like titanium dioxide and zinc oxide, sequestrants like disodium ethylenediaminetetraacetic acid, sugars like glucose and fructose, alkaline materials like calcium hydroxide, calcium carbonate, potassium hydroxide, aluminum hydroxide, and sodium hydroxide, polysaccharides like starches and modified starches, xanthan gum, cellulose powders and modified cellulose powders, ethocell, methocell, pectins, chitins, clays and modified clays like hectorite, bentonite, and lamponite, natural and synthetic zeolites, and other materials like sodium silicate, sodium benzoate, potassium silicate, silica, sodium carbonate, sodium hydrogen carbonate, barium carbonate, glycoproteins, guar gum, dextrin and modified dextrins, dextran and modified dextrans, sodium alginate, gelatin, barium silicate, calcium silicate, aluminum silicate, and aluminum oxide.

The different pace of the color change for multiple volume indicators may also be achieved by hindering the color change of the subsequent indicators after the first urination. For example, possible ways include increasing the thickness of the subsequent indicator's stationary color layer, moving the subsequent indicators further away from the "pee point" of the wearer, increasing the amount or concentration of the subsequent indicator's masking layer water soluble colorants, or incorporating the subsequent indicator's masking layer colorant into a lower polarity and more lipophilic surfactant such as steareth-2, beheneth-2, or performathox 420 to slow migration into the core Barrier Layer In some embodiments, a volume indicator may comprise a masking layer and a barrier layer. That is, a particular volume indicator may comprise both a masking layer and a barrier layer, or an article may comprise multiple volume indicators in which one comprises a masking layer and another comprises a barrier layer.

Figure 3:
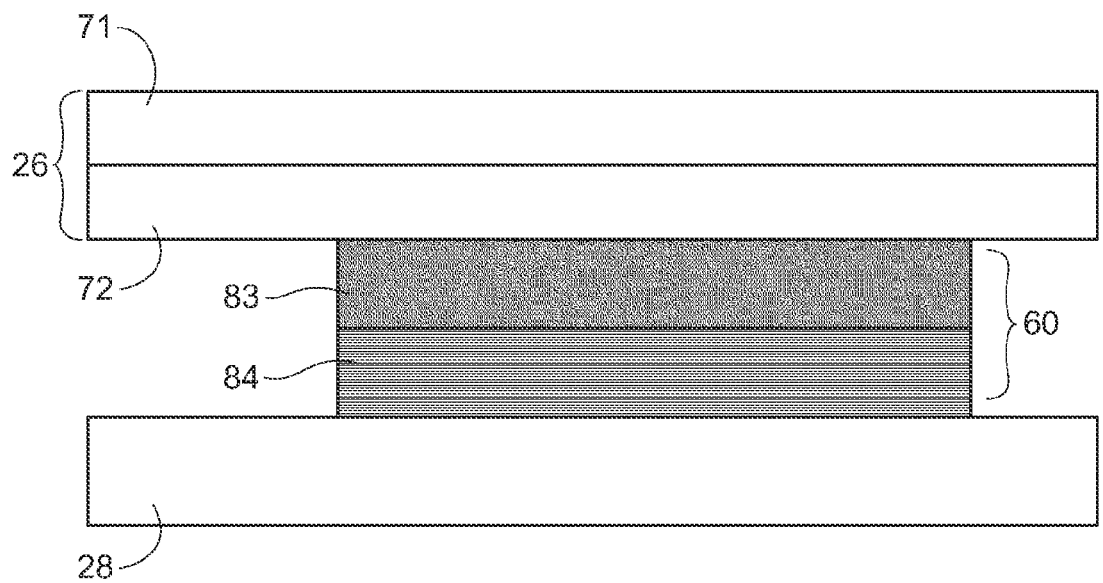
FIG. 3 shows an embodiment of a volume indicator of the present invention.

FIG. 3 is a schematic of the layers of an absorbent article comprising a volume indicator comprising a barrier layer. The outermost surface of the backsheet/outer cover 26 forms the garment contacting surface. Farthest away from the wearer is the outer cover nonwoven. Next to the outer cover nonwoven is the backsheet film. The next layer towards the interior of the article is the volume indicator, 60, comprising water-activatable colorant layer 83 and a barrier layer, 84. The water-activatable colorant layer, 83, is next to the backsheet film and closer to the wearer. A water-activatable colorant is one that is capable of changing colors when exposed to some level of liquid or water. Adjacent or next to the water-activatable colorant layer is the barrier layer, 84. The barrier layer may be any color or may be colorless. Further in from the barrier layer towards the interior of the absorbent article is the absorbent core 28.

The barrier layer may be any material capable of initially barring a liquid. The strength or longevity of the barrier before it no longer serves to bar a liquid may be dependent on time, the volume of the liquid, and/or the thickness and/or composition and/or design and/or placement/location of the barrier layer. In some embodiments, the barrier layer may be an encapsulant that completely surrounds the water-activated colorant. The basic mechanism of what happens when an insult occurs may be as follows. Upon insult, the urine is gathered in the article's absorbent core. As the core becomes wet, the wetness permeates into the volume indicator, that is, first into the barrier layer of the volume indicator. As the barrier layer is broken and/or penetrated by the wetness, the water-activatable colorant is activated and begins to change to its final color. The indicator may not completely change colors the instant any amount of liquid comes in contact with it, but rather the change of color of the volume indicator may be gradual and occur at the same pace that the barrier layer is compromised. The initial color of the volume indicator may be the initial color or design of the water-activatable colorant or the masking layer, and the final color may be the final color of the water-activatable colorant. In some embodiments, if the barrier layer has a water-soluble colorant, the color of the volume indicator, as viewed from the exterior of the article, may initially be a combination of the barrier layer color and the initial color of the water-activatable colorant and gradually become the final color of the water-activatable colorant, for example, as the barrier layer color is eroded and/or leaches and its color has less and less impact on the ensuing viewable color.

The water-activatable colorant may initially be any color. The water-activatable colorant may be a pH indicator. In some embodiments, the barrier layer may comprise a water-soluble colorant or pH indicator wherein the initial color of the volume indicator may be a combination of the water-activatable colorant or pH indicator in the barrier layer and the color of the colorant in the water-activatable colorant layer. The water-activatable colorant may be mixed with a permanent colorant. The barrier layer may be colorless, such as a clear wax, or may be made to appear white by using a white wax, and thus may not contribute to the volume indicator's initial or final color.

The initial color in the dry state of the article will depend on the concentration of colorants used in each layer, the composition of each layer, the thicknesses of those layers, design of those layers and placement of the layers. After wetness is introduced to the volume indicator, the water-soluble colorant component of the barrier layer may be absorbed into the core, and the final color of the volume indicator may be that of the colorant within the water-activatable colorant layer.

The water-activatable colorant layer may be a wetness indicator hot-melt adhesive composition (such as those described in U.S. Pat. No. 6,772,708) with bromocresol green as the pH indicator colorant where it is yellow in its acidic dry state and greenish blue when wetted with urine at a pH above 5. Its permanence in this water-activatable colorant layer would be influenced by the hydrophilicity of this water-activatable colorant layer where a more hydrophobic/lipophilic nature would inhibit the migration of the bromocresol green pH indicator since it would not be as wettable with hydrophilic exudates like urine. This lipophilicity could be increased by the inclusion of lipophilic materials like waxes (e.g. paraffinic waxes, microcrystalline waxes, synthetic waxes, natural waxes like beeswax or polyethylene waxes), mineral oils, petrolatums, fatty alcohols like stearyl alcohol or behenyl alcohol, esters like stearyl stearate, or lipophilic polymers like polyethylene vinyl acetate and polypropylene. Or, lipophilic emulsifiers like Steareth-2, Ceteth-2 or Ceteareth-2 could be included to modify and change the wetting rate with exudates like urine. In addition, the inclusion of quaternary ammonium compounds could be beneficial in preventing the migration of colorants like bromocresol green after it changes color after being wet out with exudates like urine. Without being bound by theory, it is hypothesized that the cationic charge of the quaternary amine can form a coecervate with the green and anionic bromocresol green molecule. Being neutral in charge and of higher molecular weight, the coecervate becomes much more lipophilic and less soluble in polar solvents like urine and more soluble in its matrix; especially if its matrix contains lipophilic components. This increases the permanence of the green coecervate complex in the water-activatable colorant layer after being contacted with exudates like urine.

If the previously described water-activatable colorant layer is applied on top of the yellow barrier layer where the yellow color in the barrier layer is created by the inclusion of a water soluble dye like FD&C Yellow #11 (CI #47000), the initial dry layer color as appearing from the outside of the diaper will be yellow. Since the barrier layer contains a urine soluble yellow dye which migrates into the core after wetting, the final color will be green due to the color change of the bromocresol green in the water-activatable colorant layer. The barrier layer could be made up of the FD&C Yellow #11 solubilized in a water soluble surfactant like Performathox 490 or Performathox 480 (from New Phase Technologies, Sugar Land, Tex.). The solubility of the FD&C Yellow #11 in the Performathox 490 could be controlled not only by the relative solubility properties of the yellow dye and its concentration, but also by changing the composition of the barrier such as by changing the polarity of the surfactant(s) and any included co-ingredients like waxes. In addition, the thickness of the barrier layer as well as its design and location will also affect the rate of diffusion of the FD&C Yellow #11 out of this barrier layer and into the core.

For an example of a multiple volume indicator system, the first urination from the wearer might be preferentially detected by using a more polar and urine-wettable composition in the barrier layer. This could be accomplished by using more water-wettable surfactants in the barrier layer and/or by including porosigens like sodium chloride in this barrier layer to create pathway voids for fluid flow after wet-out by the urine. A porosigen is a very hydrophilic material that remains dispersed as a solid after dispersion within its matrix. After being contacted by a hydrophilic exudate like urine, the porosigen within the matrix dissolves or wets out to create voids or fluid pathways for more efficient flow of the exudates within the matrix.

Conversely, the second volume indicator placed next to the more wettable first volume indicator could be made less wettable by eliminating the use of polar porosigens like sodium chloride or incorporating the urine soluble yellow dye in a more lipophilic matrix with less wettable surfactants or by the addition of lipophilic materials like waxes. The inclusion of lipophilic ingredients like waxes would also slow the wetting of the barrier layer to make it less susceptible to color changing after the first urination. Of course, the thickness of the barrier layer, concentration of soluble dyes in this layer, and inclusion of lipophilic ingredients will all influence the wettability of the barrier layer and ultimate color change within the water-activatable colorant layer which contains, for example, the bromocresol green pH colorant indicator. The rate of the color change of the bromocresol green within the water-activatable colorant layer containing the bromocresol green can be influenced not only by changing the thickness of this layer, but by changing the surfactant composition, inclusion of optional ingredients like acids and quaternary ammonium materials which primarily serves to reduce the migration of the anionic and green bromocresol green pH indicator colorant after it is contacted by the urine.

The barrier layer could also be made to contain a white opacifier like zinc oxide or sodium aluminosilicate or titanium dioxide where this white background created by the sodium aluminosilicate would lighten up the dry state color created by the yellow color of the bromocresol green in the in the water-activatable colorant layer. Upon wetting with urine, the sodium aluminosilicate, zinc oxide, or titanium dioxide becomes more translucent, or partially migrates into the core, such that the greenish-blue color of the bromocresol green is not lightened to the same extent as in the dry state. This delivers more contrast between the light yellow color in the dry state and the greenish-blue color in the wet state. In addition, the migration of the exudate through the barrier layer could be sped up by adding porosigens like calcium carbonate to create void spaces and pathways for fluid flow after wetting from urine/exudates. Some representative examples of porosigens that can be utilized include titanium dioxide, calcium carbonate, calcium hydroxide, sodium silicate, sodium chloride, potassium silicate, silica, starch, ethocell, methocell, barium carbonate, barium silicate, calcium silicate, aluminum silicate, aluminum hydroxide, and aluminum oxide.

Also, a cationic quaternary ammonium compound could be formulated into the barrier layer if the colorant within this barrier layer is neutral or cationic in nature. This neutral or cationic charge on the colorant within the barrier layer would not form a coecervate with the cationic quaternary ammonium compound. But, the presence of the cationic quaternary ammonium compound would impede migration of a stray anionic colorant, like the green and anionic bromocresol green, from the water-activatable colorant layer. Thus, a cationic quaternary ammonium compound in both the water-activatable colorant layer and the barrier layer would further insure limited migration of an anionic colorant like the green and anionic bromocresol green within the water-activatable colorant layer.

Controlled release technology is a known means of slowly delivering a small amount of a compound over a given time period or at a specific time based on a desired stimulus. In the present invention, controlled release technology may be used as a method to slow the color change of a volume indicator. One embodiment involves the use of colorants that are encapsulated with a thin polymer or starch coating to form small particles or beads. These capsules, which may vary in size from tens of microns to millimeters, may or may not be incorporated into a polymer coating material, such as polymethyl methacrylate or polyvinyl acrylate ester or starch, or hot melt adhesive compositions to act as an additional diffusion barrier to prevent colorant release in humid or moist environments.

A microcapsule contains an outer coating used to enclose a liquid or solid material within a small particle. The IUPAC definition of a microcapsule is a hollow microparticle composed of a solid shell surrounding a core-forming space available to permanently or temporarily entrapped substances. Microcapsules are generally in the range of 0.01 microns to hundreds of microns in diameter. Encapsulation approaches have been used for a number of applications in which a compound must be slowly but systematically released to an environment under the desired conditions. Examples include microcapsules in drug delivery, vitalizing nutrients or proteins in time release cosmetic products and fertilizers or pesticides for agricultural products. Encapsulation of the colorants may be done as it is known to those of skill in the art. Encapsulated dyes and colorants may be like those described in U.S. Pat. No. 6,358,160.

The coating may consist of a broad range of potential polymers and modified polymers like acrylate based polymers or polystyrenes, biopolymers modified biopolymers like starches and modified starches, chitosans and modified chitosans, and gums and exudated gums. The basis for most controlled release technology is the slow diffusion of the encapsulated product through the coating or matrix and into the surrounding environments. The driving force for diffusion is mass transfer from the highly concentrated interior to the dilute exterior regions. The diffusion process is often accelerated or activated by the presence of a solvent that swells or partially solvates the polymer film, thus plasticizing the polymer film and increasing the effective diffusivity of the polymer matrix. Or the microcapsule shell may simply dissolve when wetted by a substance which can solubilize the shell of the microcapsule. For example, urine could dissolve shell materials made of starches or modified starches. If there is partial or full solubilization of the shell material, the result is a faster rate of transport of the encapsulated material out of the microcapsule.

As the encapsulated dye or colorant in the barrier layer is exposed to body exudates, such as urine, the exudate may cause the diffusion of the encapsulated colorant out of its protective encapsulation shell. In other embodiments, the exudate may cause the dissolution of the shell coating of the microcapsule, resulting in the release of the encapsulated colorant.

For microcapsules, a second route to a controlled release system is the slow dissolution of an uncrosslinked or linear polymer microcapsule shell coating in a good solvent, resulting in the release of the encapsulated compound as the coating walls become thinner and ultimately dissolve completely. In this case, the dissolution rate of the polymer, rather than the diffusion rate alone, is the rate determining step in the release of the encapsulant.

A third approach to the controlled release of a material is macro-encapsulation. In this case, the material like a colorant is slowly released from a continuous polymer matrix, which may be molded into any number of shapes or objects. The primary difference between this approach and that of microencapsulation is that in the latter, the material is enclosed in well-defined microspheres on the order of magnitude of several microns, whereas in macroencapsulation, the material of interest is directly enclosed in an object of the order of magnitude of centimeters and greater. Both of these approaches involve the slow diffusion of the material out of the matrix or the encapsulant shell. In one embodiment, there may be an encapsulate within an encapsulate, wherein the outer shell is hydrophilic and dissolves quickly to release colorant whereas the inner shell is made up of a slowly soluble surfactant that ultimately releases a colorant within its shell. In certain instances, it may be advantageous to make one microcapsule with a particular colorant and particular shell solubility and encapsulate it into another microcapsule with a different colorant consisting of a shell with a unique shell solubility.

A number of different polymers and blends of polymers may be used for the barrier layer, either as a discrete or substantially flat layer, or as an encapsulation coating. Such barrier layer materials include polymethyl methacrylate, polymethacrylic acid, polyacrylic acid, polyacrylates, copolymers of ethylene and acrylic acid, copolymers of propylene and acrylic acid, polyvacrylamide, polyacryldextran, polyalkyl cyanoacrylate, cellulose acetate, cellulose acetate butyrate, cellulose nitrate, methyl cellulose and other cellulose derivates, nylon 6,10, nylon 6,6, nylon 6, polyterephthalamide and other polyamides, polycaprolactones, polydimethylsiloxanes and other siloxanets, aliphatic and aromatic polyesters, polyethylene oxide, polyethylene-vinyl acetate, polyglycolic acid, polylactic acid and copolymers, poly (methyl vinyl ether/maleic anhydride), polystyrene, polyvinyl acetate phthalate, polyvinyl alcohol) polyvinylpyrrollidone, shellac, starch and modified starches, chitosans, fatty alcohols, primary alcohols of long carbon chain lengths of C24 to C50, ethoxylated fatty alcohols, ethoxylated primary alcohols of chainlengths of C24 to C50, faty acids, and waxes such as paraffinic and microcrystalline and synthetic waxes, natural waxes like beeswax, carnauba wax and mixtures thereof.

Polymers and other shell materials used for the microcapsules should have a near zero diffusivity of the colorant through the shell material in the absence of water. Upon the introduction of water, or exudates like urine, in the surrounding matrix and the subsequent diffusion of water through the polymer film or other shell materials, the diffusivity of the polymer coating for the colorant molecules increases, allowing transport of the colorant across the polymer film shell. The ideal polymer systems for this application are those which have a limited permeability to water and thus provide a longer range of diffusion times before releasing the colorant. Such polymers could be crosslinked or uncrosslinked blends of a hydrophobic and a hydrophilic polymers, segmented or block copolymer films with a hydrophilic block or polymers which are not soluble in water. Such polymers include nylons such as nylon 6,10 or nylon 6, polyacrylonitrile, polyethylene terephthalate (PET), or polyvinyl chloride. More water permeable polymers which may be blended with hydrophobic polymers to adjust the colorant and water permeability coefficients of the film include cellulose derivatives, starch and modified starch derivatives, polyacrylates, polyethylene oxides, polyglycerols, polydimethyl siloxane and polyvinylalcohol.

Colorants that may be used include water-soluble colorants, pH indicators, and permanent colorants, and may vary from a broad range of industrial dye materials. If the colorant is encapsulated and not initially visible, the colorant may be a water-activatable colorant or a permanent colorant, but typically not a water-soluble colorant. Ideally, the dye should be compatible with the polymer used for the shell or mantle underneath the dye-encapsulant coating. Ionic and a number of water soluble dyes would be particularly compatible with ionomer materials commonly used in such mantles due to the presence of carboxylate and carboxylic acid groups in the polymer. Some dye systems change color in the presence of more polar solvents. This effect may be useful if the dye has very little color until exposed to water. Some potential dyes for this application might include merocyanine dyes and pyridinium-N-phenoxide dyes. Examples may include Napthalene Orange G, Crystal Violet, CI Disperse Red and a number of other common industrial dyes. Colorants of larger molecular weight may be desirable, as higher molecular weight colorants diffuse more slowly through a polymer matrix. Colorants could be derivatized with sulfates/sulfonates to be more water soluble or with alkyl groups to be more surfactant-like. The colorants may be modified with functional groups to make them more or less soluble in the matrix, to change their color hue, and/or to make them more or less soluble in the exudates.

Figure 4:
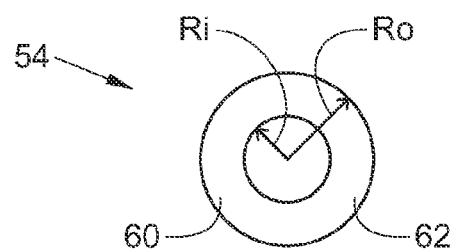
FIG. 4 shows a schematic of a dye capsule present in an embodiment of a volume indicator of the present invention.

Prior to water exposure, the water-soluble dye may be enclosed by a rigid solid polymer shell film, which is immersed in a nonaqueous medium, with a very low driving force and a high resistance to diffusion through the coating. Upon exposure to water for long time periods, water will slowly diffuse into the polymer layer and then though the microcapsule to the colorant particles. The colorant could either diffuse out of the encapsulant shell or the encapsulant shell could slowly dissolve in water exposing the colorant to the environment. The diffusion of the dye out of the polymer layer can be modeled using basic mass transfer laws. FIG. 4 is a schematic of a dye capsule 54. The dye particle 62 is surrounded by the microcapsule 60. The dye capsule has a radius of Ri, while the entire microcapsule has a radius of Ro. The rate at which dye diffuses out of the capsule is related to Ro and Ri for a dye capsule which encapsulates a dye particle. Fick's first law is commonly used to model the diffusion process. At steady state, the mass transfer of dye from the microcapsule can be modeled using the following equation: $dM/dt = 4\Pi D K \Delta C (RoRi/(Ro-Ri))$ where dM/dt is the rate of transfer of dye with time, D is the diffusivity of the dye in the polymer layer, K is the solubility of the dye in the layer, C is the concentration difference of the dye in the microcapsule versus the exterior capsule, Ro is the outer diameter and Ri is the inner diameter of the capsule.

For a layer that is about 20 to about 1000 microns in thickness, the time for diffusion of half of the dye through a polymer film such as nylon could range from about 30 minutes to about 12 hours, depending on the relative solubility of the dye in the matrix. The diffusion times can be tailored using various polymers or polymer blends, as well as different materials.

The formation of capsules may be done using a number of technologies. These technologies include polymer coacervation/phase separation using the agitation of colloidal suspensions of insoluble polymer and subsequent isolation of microparticles in a nonaqueous medium, as is known in the art. Other microcapsule formation techniques include spray drying, pan coating and centrifugal extrusion along with others. Polyamide and some polyester and polyurethane coatings may be formed using interfacial polymerization, using stabilizers to form stabilized emulsions. Bead suspension polymerization techniques, again using nonaqueous nonsolvent medium, may be used for a number of polymers achieved through free radical polymerization of vinyl polymers such as polyacrylates or acetates, or copolymers. It may be necessary to hide the color of the colorant in the encapsulant shell if the polymer coating is very transparent. In this case, the incorporation of white pigment in the polymer coating wall can be introduced during the encapsulation process.

Multiple Volume Indicators

In some embodiments, there may be more than one volume indicator. An article may have multiple volume indicators wherein all volume indicators comprise a masking layer, or wherein all volume indicators comprise a barrier layer. In some embodiments, there may be a volume indicator(s) with a masking layer and a separate volume indicator(s) with a barrier layer. In some embodiments, one or more volume indicator may be a simple pH indicator while other volume indicator(s) comprise a masking and/or barrier layer. In some embodiments, there may be a single volume indicator that comprises a barrier layer and a masking layer, or multiple volume indicators in which one comprises a masking layer and one comprises a barrier layer, or some combination thereof.

In some embodiments, the first and second volume indicators may have the same colorants in their respective masking layers and stationary color layers, but different relative amounts and/or different compositions and/or different thicknesses and/or different designs and/or different placements/locations of the masking and stationary color layers. When the article is insulted, the first volume indicator may begin to change colors quickly, that is, the masking layer colorant may quickly be absorbed into the core, while the second volume indicator may require more time and/or volume to complete its color change. In some embodiments, it might require several insults to fully change the color of the second volume indicator.

In terms of time, in some embodiments, the first volume indicator may fully change from its initial color to its final color in at most about 15-30 minutes, while the second volume indicator may fully change from its initial color to its final color only after at least about 1 hour. That is, there could be a time difference in color change of the two volume indicators. One could be a quick change to indicate some wetness while the other could be a delayed change to indicate that the user has been sitting in a wet article for a long duration or in a higher volume of fluid. In some embodiments, the first volume indicator may be completely changed to its final color state before the second volume indicator begins its color change. The thickness of any particular masking layer may vary from about 20 microns to about 1000 microns.

In some embodiments, the masking layers comprise the same colorants and composition of co-ingredients, while in other embodiments, the masking layers may be or comprise different colorants and/or different compositions and/or different thicknesses and/or different designs and/or different placements/locations. If the first and second volume indicators comprise the same masking layer and stationary color layer colorants, then eventually both indicators will have the same appearance, although the timing to arrive at the final appearance may vary due to a thicker masking layer or the inclusion of a surfactant to increase the rate of the color change after contact with the exudates or placement in a location to be wetted more readily by the exudate, for example. If the first and second volume indicators comprise either different masking layer colorants or different stationary color layer colorants, then the initial and/or final appearance of the two indicators may be different. In some embodiments, the masking layers of the first and second volume indicators may be different, providing an initial different appearance for the two volume indicators. In some embodiments, only the stationary color layer colorants may be different, thus providing different final appearances for the indicators. In some embodiments, the first volume indicator may be only a pH indicator in a hotmelt adhesive type matrix or a film forming ink type matrix (similar to wetness indicators currently known in the art) or only an ink matrix (such as commercially available inks like Aquadestruct by Sun Chemical), or comprising a water soluble colorant formulated into an acrylic or styrene-acrylic polymer which may optionally contain an emulsifier or surfactant, while only the second volume indicator comprises a masking layer.

In some embodiments, any particular volume indicator may have a noticeable color change for each 30 minutes or 1 hour after the initial insult until it reaches its final color, which in some embodiments, can be up to and over about 2 hours, about 2.5 hours, about 3 hours, about 3.5 hours, about 4 hours, 8 hours, 12 hours, or any half-hour interval between about 2 and about 12 hours. Similarly, in some embodiments, any particular volume indicator may have a noticeable color change for each 50-75 mls (milliliters) of exudate that it is exposed to, up to about 150 mls or about 300 mls. In some embodiments, a first volume indicator may change to its final appearance with exposure to a minimum of about 20 mls (such a first indicator may be a pH based indicator), while the second volume indicator may not begin any color change until it is exposed to at least about 100 mls. The time that the second volume indicator takes to complete its color change may be controlled by either the total time that it is exposed to a minimum amount of insult, the total time that it is exposed to any insult, or may be controlled by the total volume to which it is exposed (e.g., after exposure to a total of about 150 mls, its color change will be complete). In some embodiments, there may be a third volume indicator. For example, a first volume indicator may change to its final appearance in at most about 15-30 minutes, letting the caregiver know that some insult has occurred. A second volume indicator may reach its final appearance after about either 1 to 2 hours of exposure to wetness or after it has been exposed to a minimum of about 100 mls. A third volume indicator may not reach its final appearance until after either exposure to a minimum of about 150 mls or after about 2 hours or longer (up to 12 hours) of wetness.

In one embodiment, an article comprises two volume indicators, each volume indicator comprising an encapsulated colorant or a barrier layer. In one embodiment, the encapsulation of the first volume indicator or the thickness of the barrier layer may be made so that when it is exposed to urine, the colorant will become visible after no more than about 5 minutes, in some embodiments, about 10, 15, 20, or 25 minutes. The encapsulation of the second volume indicator or the thickness of the barrier layer in the second volume indicator may be made so that the colorant will not be visible until at least about 1 hour after exposure to urine, or in some embodiments, about 2 hours, about 2.5 hours, about 3, about 3.5 hours, or about 4 hours up to 12 hours.

In some embodiments, the first volume indicator colorant(s) and the second volume indicator colorant(s) may be the same. In some embodiments, they may be different. In some embodiments, the first volume indicator changes from a first color to a second color, while the second volume indicator changes from a third color to a fourth color. In some embodiments, the second volume indicator may not be triggered (meaning the final color state is visible) despite more than one insult.

Figure 5A:
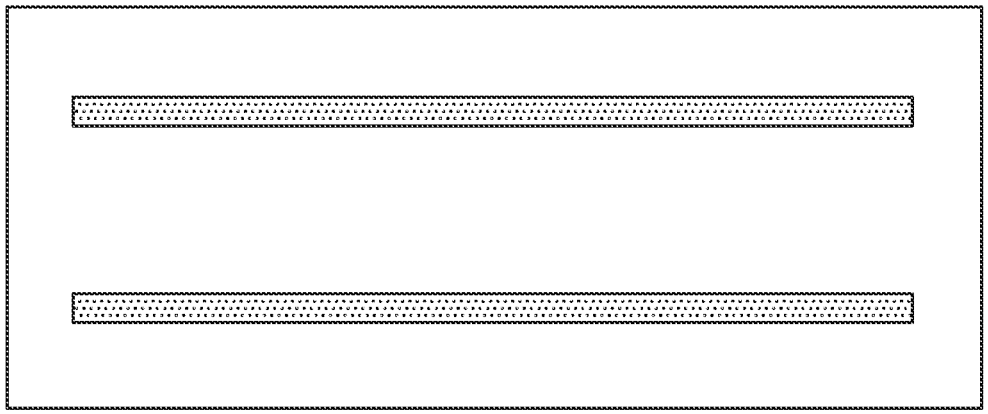
FIGS. 5a, 5b, and 5c are schematics of multiple volume indicators as they are exposed to wetness.
Figure 5B:
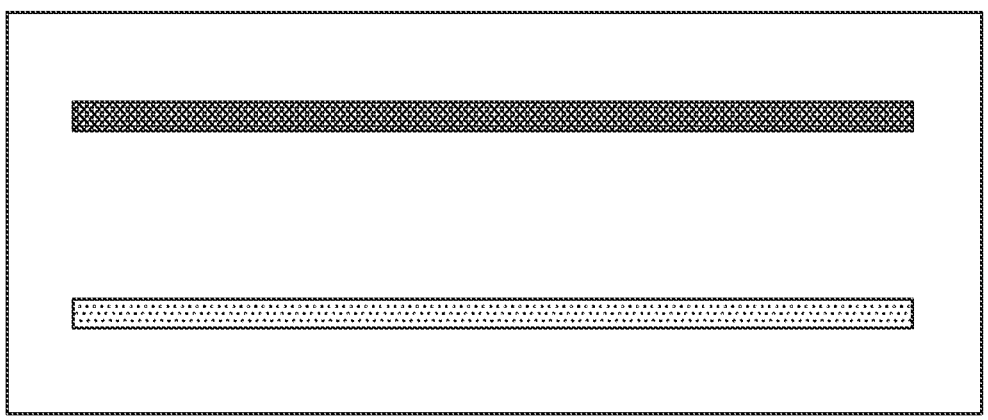
Figure 5C:
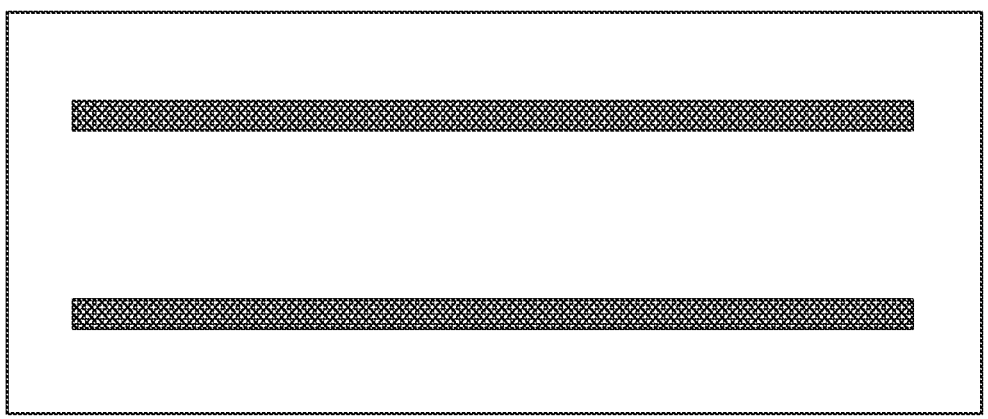

FIGS. 5A, 5B, and 5C illustrate embodiments of a dual volume indicator. FIG. 5A shows the initial, dry state appearance of two volume indicators. The initial colors may be the same color, or they may be different. FIG. 5B shows what the two indicators may look like after about 15 minutes or a light load of exudates (about 15 to about 30 ml) has been released into the article. One indicator remains in its initial color, while the other has changed into its final color state. FIG. 5C shows the two volume indicators after at least one hour of exposure to body exudates or may also represent the two volume indicators after heavy loads of body exudates (greater than about 75 ml).

Figure 6A:
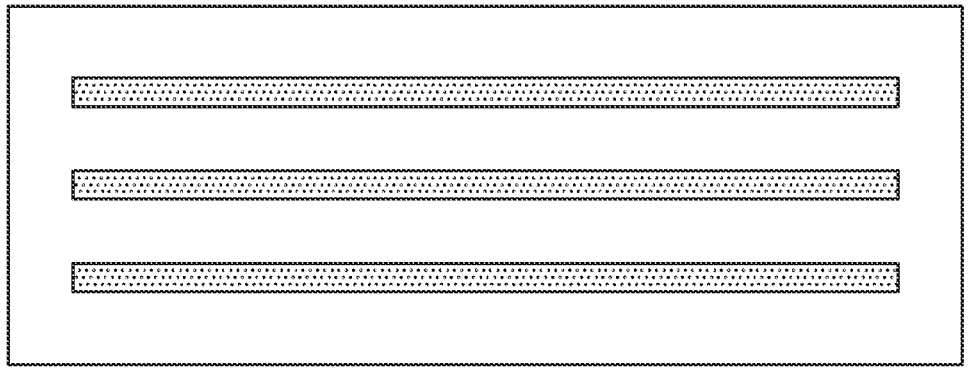
FIGS. 6a, 6b, 6c, and 6d are schematics of multiple volume indicators as they are exposed to wetness.
Figure 6B:
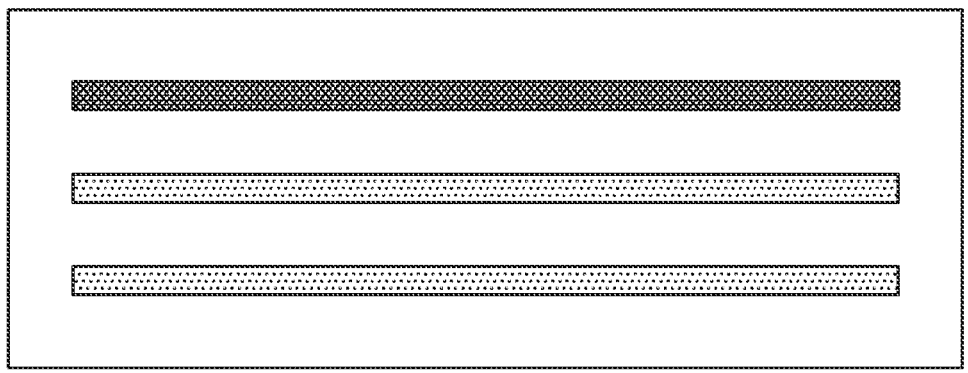
Figure 6C:
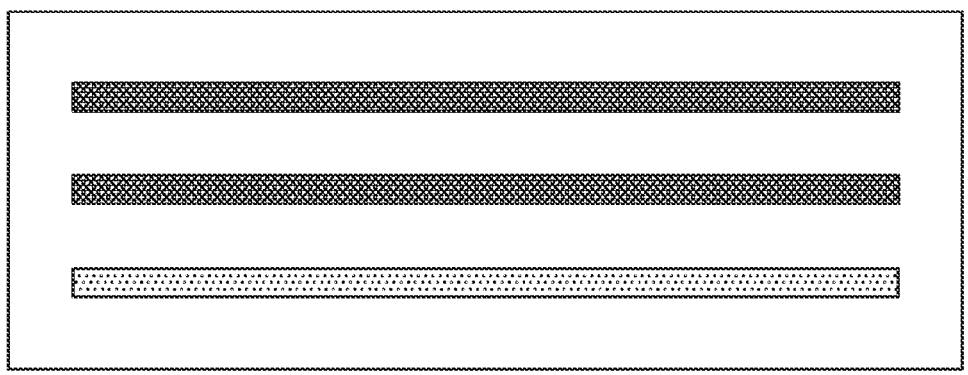
Figure 6D:
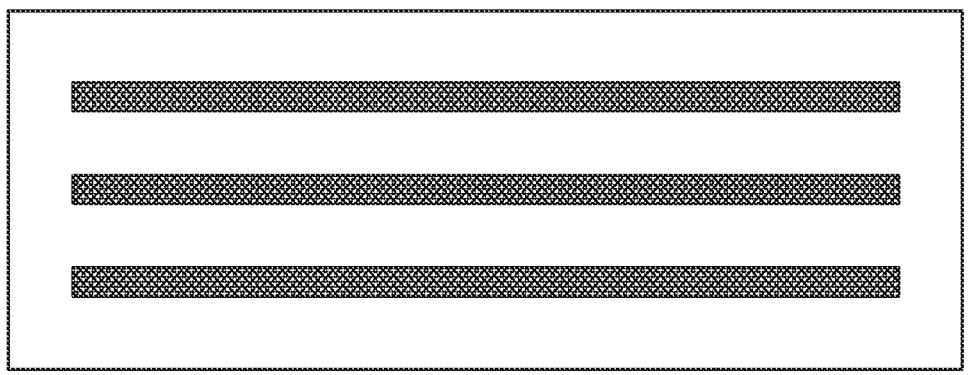

FIGS. 6A, 6B, 6C, and 6D illustrate embodiments of a triple volume indicator. FIG. 6A shows the initial, dry state appearance of three volume indicators. The initial colors may be the same color, or they may be some combination of different colors. FIG. 6B shows what the three indicators may look like after about 15 minutes or a light load (about 15 to about 30 ml) of exudates has been released into the article. Two indicators remain in their initial colors, while one indicator has changed into its final color state. FIG. 6C shows what the three indicators may look like after about 30 minutes to about 2 hours, or after a medium load of body exudates (about 50 to about 70 ml). Two of the indicators have changed to their final color state, while one remains unchanged. FIG. 6D shows what the three indicators may look like after at least about 2 hours or after heavy loads of body exudates (greater than about 75 ml). Either circumstance triggers all three indicators and all three are in their final color state. The three indicators may start with the same initial color but then each change into different colors upon activation. For the purpose of illustration in this example, stripe patterns have been used, but it is noted that the indicators can be in various graphical or geometric patterns as described below. If desired for effective performance, the volume indicators may also be placed in different locations within the absorbent article in order to vary their contact with the exudate.

The placement of the volume indicators on the article can be done in any way, with any spacing wanted. The volume indicators may be in discrete or continuous patterns, or may form numbers indicating hours, etc., for example. In various embodiments an indicator can have an overall shape that is more or less elongated. In some embodiments, part, or parts, or all of an indicator and/or an indicating area can be straight, curved, angled, segmented, or any regular or irregular geometric shape (such as a square, rectangle, triangle, trapezoid, octagon, hexagon, star, half circle, a quarter circle, a half oval, a quarter oval, a radial pattern, or a professional sports team logo, such as a "G" of the Green Bay Packers, etc.), a recognizable image (such as a letter, number, word, character, face of an animal, face of a person, etc.), or another recognizable image (such as a plant, a car, etc.), or another shape, or combinations of any of these shapes. Also, in various embodiments, an indicator can have varying widths over part, or parts, or all of its length.

A volume indicator may be located at any point in the absorbent article likely to be contacted by exudates from the wearer. For example, in one embodiment, a volume indicator may be located in the portion of the article in communication with the urine loading point (i.e., the location in which the urine typically insults the article, such as in the vicinity of the longitudinal centerline 100 of the article in the crotch region 37 of the article). In addition, a volume indicator may be attached to any component of the article, but should be in communication with the urine loading point, including, but not limited to, via capillary actions or conductive links. For example, a volume indicator may be attached to the topsheet, the absorbent core, or the backsheet. In one embodiment, at least one volume indicator may be positioned between the backsheet and the absorbent core, such that the colors of the volume indicator can be seen through at least a portion of the backsheet. In one embodiment, at least one volume indicator may be disposed within the absorbent core.

Colorants

A colorant may be, for example, a dye, an ink, a pigment, or a pH indicator. A water-activated colorant can be soluble within the volume indicators and in certain cases, it can be suitable to homogeneously suspend or disperse the solid state of the colorant within the volume indicator. As noted, the water-activatable colorant changes color upon coming in contact with water or urine. In some embodiments, the volume indicator may further comprise a permanent colorant that does not change color upon coming in contact with water or urine.

Some representative examples of water-activated colorants that can be used in the practice of this invention include: Malachite green, brilliant green, crystal violet, erythrosine B, methyl green, methyl violet 2D, picric acid, naphthol yellow S, quinaldine red, eosine Y, metanil yellow, m-cresol purple, thymol blue, xylenol blue, basis fuchsin, eosin B, 4-p-aminophenol(azo)benzenesulphonic acid-sodium salt, cresol red, martius yellow, phloxine B, acid Phloxine B, methyl yellow, bromophenol blue, methylene blue, congo red, methyl orange, bromochlorophenol blue (water soluble or free acid form), ethyl orange, flourocene WS, bromocresol green, chrysoidine, methyl red sodium salt, alizarine red S—H2O, cochineal, chlorophenol red, bromocresol purple, 4-naphtha, alizarin, nitrazine yellow, bromothymol blue, brilliant yellow, neutral red, rosalic acid, phenol red, 3-nitro phenol, orange II, phenolphthalein, o-cresolphthalein, nile blue A, thymolphthalein, aniline blue WS, alizarine yellow GG, mordant orange, tropaolin O, orange G, acid fuchsin, thiazol yellow G, indigo carmine, cresol red, methyl red, p-nitrophenol, and alizarin yellow R. In certain instances, it is advantageous to use the free acid form, free base form, or salt form of the colorants, or mixtures thereof.

Water-soluble colorants may include the FD&C and D&C colorants like FD&C Blue No. 1, FD&C Blue No. 2, FD&C Green No. 3, FD&C Red No. 40, FD&C Red No. 4, FD&C Yellow No. 5, FD&C Yellow No. 6, C.I. Food Blue 5, and C.I. Food Red 7, D&C Yellow No. 10, D&C Yellow No. 7, D&C Yellow No. 2, D&C Yellow No. 8, D&C Orange No. 4, D&C Red No. 22, D&C Red No. 28, D&C Red No. 33, D&C Green No. 8, D&C Green No. 5, D&C Brown No. 1, and any combination thereof. Preferably, the colorant is soluble within the volume indicator, but, as noted in certain instances, the colorant can function as intended by homogeneously suspending or dispersing its solid state form within the volume indicator or some of the colorant could be partially solubilized with its remainder being dispersed and insoluble within the matrix.

Additional suitable fluid colorants include water soluble colorants like direct dyes, acid dyes, base dyes, and various solvent-soluble colorants. Dispersed or suspended pigment colorants can also be employed into these volume indicators. Examples include, but are not limited to, C.I. Acid Yellow 73, C.I. Solvent Yellow 94, C.I. Acid Yellow 74, C.I. Solvent Orange 32, C.I. Solvent Red 42, C.I. Acid Orange 11, C.I. Solvent Red 72, C.I. Pigment Orange 39, C.I. Solvent Orange 18, C.I. Acid Red 87, C.I. Solvent Red 43, C.I. Pigment Red 90:1, C.I. Solvent Red 44, C.I. Solvent Red 45, C.I. Solvent Orange 16, C.I. Acid Red 91, C.I. Acid Red 98, C.I. Acid Red 92, C.I. Solvent Red 48, C.I. Pigment Red 174, C.I. Acid Red 95, C.I. Solvent Red 73, C.I. Pigment Red 191, C.I. Acid Red 51, C.I. Food Red 14, C.I. Pigment Red 172, C.I. Solvent Red 140, C.I. Acid Red 93, C.I. Solvent Red 47, C.I. Acid Red 94, C.I. Solvent Red 141, C.I. Mordant Violet 25, C.I. Solvent Orange 17, C.I. Solvent Red 46, D&C Red 27 (C.I. 45410:1), D&C Orange 5 (C.I. 45370:2), and combinations thereof. More preferred colorants are selected from the group consisting of D&C Red 27, D&C Orange 5, and combinations thereof.

Additional suitable colorants may include bromopyrogallol red, bromoxylenol blue, methylene blue, monoazo dyes such as acid alizarin voliet N, monoazo pyrazoline dyes (such as acid yellow 34), diazo dyes (such as acid black 24), anthraquinone dyes (such as acid black 48), amphoteric anthraquinone dyes (such as acid blue 45), triphenylmethane dyes (such as acid fuchsin), phthalein type dyes (such as o-cresolphthalein), xanthene dyes (such as 2'7' dichlorofluorescein eosin B), heterocyclic acridine aromatics (such as cridine range), diphenulmethane dyes (such as auramine O), triphenylmethane dyes (such as basic fuchsin), cationic thiazine dyes (azure C), cationic anthraquinone dyes such as basic blue 47, phthalocyanine type dyes (such as strazon orange G), anthraquinone type (sch as alizarin), neutral complex dyes (such as azure A eosinate), terpene type dyes (such as trans-beta-carotene), as well as combinations including at least one of the foregoing dyes. Examples of colorants further include, but are not limited to, organic dyes, inorganic pigments, colored macromolecules, colored nanoparticles and materials. Examples of dyes include acridine dyes, anthraquinone dyes, arylmethane dyes, azo dyes, nitro dyes, nitroso dyes, phthalocyanine dyes, quinoneimine dyes, Aazin dyes, Indophenol dyes, oxazin dyes, Oxazone dyes, Thiazole dyes, xanthene dyes, Fluorene dyes, fluorone dyes, rhodamine dyes. Examples of pigments include Cadmium pigments: cadmium yellow, cadmium red, cadmium green, cadmium orange; Carbon pigments: carbon black (including vine blac, lamp black), ivory black (bone char); Chromium pigments: chrome yellow and chrome green; Cobalt pigments: cobalt violet, cobalt blue, cerulean blue, aureolin (cobalt yellow); Copper pigments: Azurite, Han purple, Han blue, Egyptian blue, Malachite, Malachite green, Calcocid Blue 2G, Paris green, Phthalocyanine Blue BN, Phthalocyanine Green G, verdigris, viridian; Iron oxide pigments: sanguine, caput mortuum, oxide red, red ochre, Venetian red, Prussian blue; Clay earth pigments (iron oxides): yellow ochre, raw sienna, burnt sienna, raw umber, burnt umber; Lead pigments: lead white, cremnitz white, Naples yellow, red lead; Mercury pigments: vermilion; Titanium pigments: titanium yellow, titanium beige, titanium white, titanium black; Ultramarine pigments: ultramarine, ultramarine green shade; Zinc pigments: zinc white, zinc ferrite. Other examples include alizarin, alizarin crimson, gamboge, cochineal red, rose madder, indigo, Indian yellow, Tyrian purple, organic quinacridone, magenta, phthalo green, phthalo blue, pigment red.

Many of these aforementioned colorants do not change colors when contacted by an aqueous solution like urine. These are referred to as permanent colorants which can function to change the color hue of the volume indicator in either its dry state or color changed state after contact with a fluid like urine. Some examples of oil soluble permanent colorants include D&C Yellow No. 11, D&C Red No. 17, D&C Red No. 21. D&C Red No. 27, D&C Violet No. 2, D&C Green No. 6, and D&C Orange No. 5. Some of these permanent colorants are oil or liposoluble and can change the color hue of the volume indicator in either the dry or wet state. But, they can be advantageous due to their reduced solubility in hydrophilic liquids like urine. Thus, their leaching into other components of the diaper is inhibited and if properly formulated, they possess a higher probability of remaining bound within the volume indicator after being wetted with an aqueous liquid like urine.

EXAMPLES

Example 1

Volume Indicator Comprising a Masking Layer and a Stationary Color Layer

The volume indicator comprises a porous stationary color layer that is a water swellable hydrogel made with acrylic polymers permanently dyed with a blue colorant. The diffusion of urine through this permanent hydrogel layer could be controlled not only by the thickness of this layer but also by the inclusion of optional ingredients like surfactants, emulsifiers, waxes, mineral oils, silicones, solid particles like clays and powders like talc and inorganic pigments like titanium dioxide, or porosigens like sodium chloride. The masking layer contains a water soluble dye like FD&C yellow #10, which has a color index number of 47005 dissolved in a polar surfactant like polyethylene (and) C20-40 Pareth-95, available as Performathox 490 from New Phase Technologies in Sugar Land, Tex., or a high molecular weight polyethylene glycols like Carbowax 8000 from Dow Chemical in Midland, Mich.

In the dry state, the thickness and/or yellow colorant concentration would be high enough to produce a dark and opaque yellow color as viewed from the outside of the diaper when the diaper is dry and before exudates have been exuded from the exudater. The urine or other exudates penetrate the stationary color layer and ultimately reach the masking layer to solubilize the FD&C yellow #10 colorant such that it migrates through the stationary color layer and into the core. Thus, upon diffusion of the yellow FD&C #10 from the masking layer into the core, the color of the volume indicator changes to the blue color of the stationary layer.

Example 2

Volume Indicator Comprising a Masking Layer and a Stationary Color Layer

The stationary color layer comprises a colored polypropylene non-woven layer with the colorant permanently and homogeneously distributed within the polypropylene non-woven fibers. Optionally, the polypropylene fibers making up this non-woven layer could be treated with a surfactant to speed up the rate of absorption of the urine from the core. The masking layer comprises any one of the following water-soluble yellow dyes, including FD&C Yellow No. 5 (=CI No. 19140), FD&C Yellow No. 6 (=CI No. 15985), Ext D&C Yellow No. 7 (=CI No. 10316), D&C Yellow No. 10 (=CI No. 47005), and D&C Yellow No. 8 (=CI No. 45350). A water-soluble yellow dye in the masking layer and a permanently blue-dyed stationary color layer creates an initial color of green with the shade of green influenced by the amount of each of the colorants as well as their relative hues. After contact with urine or exudates, the yellow of the masking layer migrates into the core, leaving a final color for the volume indicator as blue.

Example 3

Volume Indicator Comprising a Barrier Layer

A volume indicator comprises a water-activatable colorant layer comprising a wetness indicator hot-melt adhesive composition with bromocresol green. The barrier layer is made up of wax comprising FD&C Yellow #11 solubilized in a water soluble and hydrophilic surfactant like Performathox 490 (from New Phase Technologies, Sugar Land, Tex.). The initial dry color as appearing from the outside of the article will be yellow. Since the barrier layer contains a urine soluble yellow dye which migrates into the core after wetting, the final color will be green due to the color change of the bromocresol green in the water-activatable colorant layer.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a topsheet, a backsheet, and an absorbent core disposed between the topsheet and the backsheet, wherein the article further comprises at least two volume indicators;
    wherein at least one volume indicator comprises a masking layer comprising a water-soluble colorant and a stationary color layer comprising a permanent colorant;
    wherein a first volume indicator with a first masking layer has a first thickness and a second volume indicator with a second masking layer has a second thickness, and wherein the second thickness is at least about two times thicker than the first thickness.

2. The absorbent article of claim 1, wherein the stationary color layer comprises a water-insoluble colorant.

3. The absorbent article of claim 1, wherein the stationary color layer comprises a pH indicator or water activatable colorant.

4. The absorbent article of claim 1, wherein the stationary color layer is between the backsheet and the absorbent core and adjacent to the absorbent core; and wherein the masking layer is between the stationary color layer and the backsheet.

5. The absorbent article of claim 1, wherein the first masking layer and the second masking layer comprise the same colorants in different amounts.

6. The absorbent article of claim 1, wherein the first masking layer and the second masking layer comprise different colorants.

7. The absorbent article of claim 1, wherein a first volume indicator changes from an initial color to a final color in at most about 30 minutes after exposure to a body exudate, and wherein a second volume indicator changes from an initial color to a final color only after at least about 1 hour of exposure to a body exudate.

8. The absorbent article of claim 7, further comprising a third volume indicator that changes from an initial color to a final color only after at least about two hours of exposure to a body exudate.

9. The absorbent article of claim 1, wherein a first volume indicator changes from an initial color to a final color after exposure to at least about 20 mls of body exudates, and wherein a second volume indicator changes from an initial color to a final color only after exposure to at least about 100 mls of body exudates.

10. The absorbent article of claim 9, further comprising a third volume indicator that changes from an initial color to a final color only after exposure to at least about 150 mls of body exudates.

11. The absorbent article of claim 1, wherein a second volume indicator changes colors after each exposure to at least about 50 mls of body exudates until total exposure of at least about 300 mls of body exudates.

12. The absorbent article of claim 1, wherein a stationary color layer comprises a porosigen.

13. An absorbent article comprising a topsheet, a backsheet, and an absorbent core disposed between the topsheet and the backsheet, wherein the article further comprises at least two volume indicators;
    wherein at least one volume indicator comprises a masking layer comprising a water-soluble colorant and a stationary color layer comprising a permanent colorant,
    wherein a first volume indicator has a first masking layer and a first stationary color layer and a second volume indicator has a second masking layer and a second stationary color layer; and the first and second masking layers comprise the same colorant and the first and second stationary color layer comprise different colorants and different amounts of porosigens.

14. The absorbent article of claim 13, wherein the first masking layer has a first thickness and the second masking layer has a second thickness, wherein the second thickness is greater than the first thickness.

15. The absorbent article of claim 13, wherein the first volume indicator changes from an initial color to a final color in at most about 30 minutes after exposure to a body exudate, and wherein the second volume indicator changes from an initial color to a final color only after at least about 1 hour of exposure to a body exudate.

16. The absorbent article of claim 13, wherein the first volume indicator changes from an initial color to a final color after exposure to at least about 20 mls of body exudates, and wherein the second volume indicator changes from an initial color to a final color only after exposure to at least about 100 mls of body exudates.

17. An absorbent article comprising a topsheet, a backsheet, and an absorbent core disposed between the topsheet and the backsheet, wherein the article further comprises at least two volume indicators;
wherein at least one volume indicator comprises a masking layer comprising a water-soluble colorant and a stationary color layer comprising a permanent colorant, wherein a first volume indicator has a first masking layer and a first stationary color layer and a second volume indicator has a second masking layer and a second stationary color layer; and the first and second masking layers comprise different colorants and the first and second stationary color layers comprise the same colorants.

18. The absorbent article of claim 17, wherein the first volume indicator changes from an initial color to a final color in at most about 30 minutes after exposure to a body exudate, and wherein the second volume indicator changes from an initial color to a final color only after at least about 1 hour of exposure to a body exudate.

19. The absorbent article of claim 17, wherein the first volume indicator changes from an initial color to a final color after exposure to at least about 20 mls of body exudates, and wherein the second volume indicator changes from an initial color to a final color only after exposure to at least about 100 mls of body exudates.

20. An absorbent article comprising a topsheet, a backsheet, and an absorbent core disposed between the topsheet and the backsheet, wherein the article further comprises at least two volume indicators;
wherein at least one volume indicator comprises a masking layer comprising a water-soluble colorant and a stationary color layer comprising a permanent colorant, wherein a first volume indicator has a first masking layer and a first stationary color layer and a second volume indicator has a second masking layer and a second stationary color layer; and the first and second masking layers comprise different colorants and the first and second stationary color layers comprise different colorants.

21. An absorbent article comprising a topsheet, a backsheet, and an absorbent core disposed between the topsheet and the backsheet, wherein the article further comprises at least two volume indicators;
wherein at least one volume indicator comprises a masking layer comprising a water-soluble colorant and a stationary color layer comprising a permanent colorant, wherein the first masking layer and the second masking layer comprise the same colorants in different amounts; and
wherein a first volume indicator with a first masking layer has a first thickness and a second volume indicator with a second masking layer has a second thickness, and wherein the second thickness is greater than the first thickness.

22. An absorbent article comprising a topsheet, a backsheet, and an absorbent core disposed between the topsheet and the backsheet, wherein the article further comprises at least two volume indicators;
wherein at least one volume indicator comprises a masking layer comprising a water-soluble colorant and a stationary color layer comprising a permanent colorant, wherein the first masking layer and the second masking layer comprise different colorants; and
wherein a first volume indicator with a first masking layer has a first thickness and a second volume indicator with a second masking layer has a second thickness, and wherein the second thickness is greater than the first thickness.

23. The absorbent article of claim 22, wherein the first volume indicator changes from an initial color to a final color in at most about 30 minutes after exposure to a body exudate, and wherein the second volume indicator changes from an initial color to a final color only after at least about 1 hour of exposure to a body exudate.

24. The absorbent article of claim 22, wherein the first volume indicator changes from an initial color to a final color after exposure to at least about 20 mls of body exudates, and wherein the second volume indicator changes from an initial color to a final color only after exposure to at least about 100 mls of body exudates.

* * * * *